United States Patent [19]
Belt

[11] 4,436,093
[45] Mar. 13, 1984

[54] CARDIAC PACER HAVING ACTIVE NOTCH FILTER SYSTEM

[75] Inventor: Kenneth W. Belt, Fort Atkinson, Wis.

[73] Assignee: Norland Corporation, Fort Atkinson, Wis.

[21] Appl. No.: 425,223

[22] Filed: Sep. 28, 1982

Related U.S. Application Data

[63] Continuation of Ser. No. 203,959, Nov. 4, 1980, abandoned.

[51] Int. Cl.$^3$ .............................................. A61N 1/36
[52] U.S. Cl. .............................. 128/419 PG; 128/901
[58] Field of Search ............... 128/696, 901, 419 PG, 128/419 PT, 704

[56] References Cited
U.S. PATENT DOCUMENTS

| | | |
|---|---|---|
| 3,848,586 | 11/1974 | Suzuki et al. ........................ 128/901 |
| 3,927,677 | 12/1975 | Gobeli et al. ........................ 128/901 |
| 4,023,564 | 5/1977 | Valiquette et al. .................. 128/704 |
| 4,114,627 | 9/1978 | Lewyn et al. ................. 128/419 PG |
| 4,244,376 | 6/1981 | Fisher et al. ........................ 128/901 |

Primary Examiner—William E. Kamm
Attorney, Agent, or Firm—Lockwood, Dewey, Alex & Cummings

[57] ABSTRACT

A battery powered external pacer operable in fixed-rate and demand modes includes a sense amplifier having an active notch filter system for attenuating power line interference. The filter system comprises four separate data channels each including a transmission gate synchronously driven by pacer clock pulses for frequency stability. Charges developed on capacitors in each data channel are summed by an output capacitor to avoid the need for amplifiers in each channel. A detector having two comparators for detecting positive and negative directed R-wave components derives heart pulses from the amplified signal. A pulse-driven reference supply having very low power consumption provides operating bias required by the detector. A battery monitor having a single comparator simultaneously monitors supply voltage for low and unusable voltage levels.

14 Claims, 13 Drawing Figures

CARDIAC PACER HAVING ACTIVE NOTCH FILTER SYSTEM

This is a continuation of application Ser. No. 203,959, filed Nov. 4, 1980 and now abandoned.

BACKGROUND OF THE INVENTION

The present invention relates generally to cardiac pacers, and more particularly to improvements in such pacers which provide increased noise immunity and reduced power consumption.

Cardiac pacers, which supply amplitude and rate-controlled electrical pulses to a patient's heart to stimulate muscle contraction, have been developed for both internal applications, wherein the pacer is implanted within the patient's body, and external applications, wherein the pacer is externally carried by the patient and rate, pulse amplitude and sensitivity are adjusted as required by the application. External pacers are typically used in emergency situations, where the patient is awaiting implant of a permanent pacer, or where the operation of other pacers is being tested or adjusted. These pacers are typically battery powered for freedom of movement, and must be designed to provide long operating life and a high degree of reliability in often adverse hospital and clinic environments.

Cardiac pacers generally operate in one of three modes: a fixed rate mode, wherein stimulation pulses are produced at a user-selected rate regardless of the occurrence of natural heart pulses; a synchronous mode, wherein stimulation pulses are produced at the end of a predetermined time period following the production of a natural heart pulse; or a demand mode, wherein stimulation pulses are produced only in the absence of a particular heart pulse.

Typically, in the demand mode heart pacers produce a stimulation pulse in the absence of a naturally occurring R-wave signal corresponding to ventricular contraction, which is detected in a sense signal derived from the heart by means of electrically conductive leads physically attached to the heart. The stimulation pulse generated by the pacer is typically applied to the ventricle of the heart by the same leads to induce a desired ventricular contraction.

In the presence of electrical interference in the form of noise or hum on the pacer leads, such as may be induced by power distribution lines or line operated electrical equipment, erroneous operation of a demand mode pacer can occur. The pacer may treat the interference as indicative of a natural heartbeat, and not generate a stimulation pulse even if one is required.

Pacers are often programmed to revert to an alternate fixed rate mode in the presence of electrical noise which prevents the reliable reception of R-wave pulses. Unfortunately, the continuous output pulse production of the pacer in the fixed rate mode undesirably increases battery drain and prevents the heart from naturally beating at its normal rhythm.

One method utilized for reducing the effects of noise and hum is the use of a bandpass filter circuit in the sense amplifier of a pacer to isolate desired R-wave and P-wave signals from undesired interference signals. Typically, such filter circuits in external pacers have bandpass characteristics centered on frequencies from 50 hertz to 150 hertz, and bandwidths of two octaves or more. Consequently, these filter circuits provide little rejection of 60 hertz and 50 hertz power line frequency signals, which are often the principal source of interference, and interference-induced inhibition of portable demand mode pacers continues to be a chronic problem.

It has been proposed that a low pass filter be provided to reject all frequencies above 35 hertz, allowing R-wave energy in the 13 hertz to 35 hertz band to pass and rejecting energy at 50 hertz and 60 hertz power line frequencies. For such a filter to be effective, approximately 25 dB attenuation at 50 and 60 hertz power line frequencies is necessary. A low-pass filter having a corner frequency of 35 hertz and 25 dB attenuation at 60 hertz typically requires at least eight poles. Unfortunately, eight pole LC filters are not practical at power line frequencies because of the size of the inductances involved, and eight pole active RC filters have heretofore required the use of undesirably large plastic dielectric capacitors. The problem is compounded in pacers for European use, which would typically require at least a thirteen pole low pass filter to achieve a corner frequency of 35 hertz and 25 dB attenuation at 50 hertz.

Another proposal is that a passive notch filter, such as a twin-T or bridged-T network, be provided at the appropriate power line frequency. Unfortunately, the notch depth and center frequency in such filters is very sensitive to component variations, such as caused by temperature changes and component aging, making their rejection of power line interference in pacer applications subject to unsatisfactory variations.

It has also been proposed that the analog signal derived from the heart be converted to digital information and then processed using digital techniques to extract the cardiac signal. This would require a complex digital system having high data rates, with attendant high power consumption, making this proposal unsuitable in a battery-powered pacer.

The present invention is directed to a cardiac pacer and sense amplifier wherein power line interference is reliably rejected by means of a high stability active notch filter system synchronously driven by the crystal oscillator of the pacer.

A requirement of battery-powered pacers, whether implanted or portable, is that they have low power consumption to prolong battery life. Previous attempts at reducing power consumption resulted in pacers wherein the pulse rate and R-wave detection threshold were subject to variation with changes in battery voltage, since the high current drain of conventional voltage regulator circuits precluded the use of a precision reference voltage source within the pacer. The present invention is further directed to a low current drain reference voltage source for use in a battery-powered cardiac pacer.

Another requirement of portable battery-powered cardiac pacers is that circuit means be provided for monitoring battery condition. Preferably, such circuit means must be compatible with the requirement of low power consumption, should not unnecessarily complicate the circuitry of the pacer so as to keep production costs at a minimum, and should interrupt operation of the pacer when the battery becomes unusable. The present invention is further directed to a battery monitor circuit which meets these requirements.

A further requirement of a portable demand-mode cardiac pacer is that R-wave signals of either positive or negative polarity be reliably detected for use by the pulse control logic circuitry of the pacer. To this end, such detector circuits must maintain a precise reference threshold above which incoming signals are identified as R-wave signals. Unfortunately, prior art detector circuits having such threshold levels have been undesirably complex. The present invention is further directed to an R-wave detector circuit for a cardiac pacer which is simple in construction and which provides a precise detection threshold above which sensed signals of either polarity are detected as R-wave signals.

Accordingly, it is a general object of the present invention to provide a new and improved cardiac pacer.

It is a more specific object of the present invention to provide a cardiac pacer having improved immunity to power line interference.

It is another specific object of the present invention to provide a cardiac pacer having reduced power consumption for extended battery life.

It is another specific object of the present invention to provide a cardiac pacer having an improved battery condition indicating circuit.

It is another specific object of the present invention to provide a cardiac pacer having improved detection capability of sensed R-wave signals.

SUMMARY OF THE INVENTION

The invention is directed, in a cardiac pacer of the type responsive to an applied cardiac sense signal which includes a desired signal component and a power line-induced interference component, to a sense amplifier which includes means comprising a plurality of selectable sample and hold channels for independently sampling the instantaneous amplitude of the cardiac signal. Sampling means are provided for sequentially and repeatedly selecting the channels whereby each channel is selected for an equal period of time over a complete selecting cycle. Signal summation means combine the outputs of the channels to derive an output signal which includes the desired signal components. The channels are selected at a frequency of nf, where n is a whole integer and f is the frequency of the power line component, whereby the interference component is attenuated in the output signal.

The invention is further directed in a cardiac pacer of the type operable from a battery which provides a reduced supply voltage with decreasing life expectancy, to a battery monitor circuit which includes a comparator amplifier which has first and second inputs and an output, the comparator producing an output upon the voltage level on the first input exceeding the voltage level applied to the second input. Means are provided for applying a reference voltage to the second input, and voltage divider means are provided for applying a first predetermined portion of the supply voltage to the first input, the divider means being responsive to an applied switching signal for alternatively applying a second predetermined portion of the supply voltage to the first input. Output circuit means provide a first alarm signal in response to an output from the comparator amplifier, and respond to an applied switching signal to alternatively produce a second alarm signal independent from the first alarm signal in response to an output from the comparator amplifier. Switching means periodically apply a switching signal to the voltage divider means and the output circuit means whereby the battery monitor circuit independently monitors the occurrence of two different supply voltage levels.

The invention is further directed, in a cardiac pacer of the type operable from a battery and requiring a reference voltage source, to a reference voltage supply circuit which includes generating means for generating a source of switching pulses of relatively short duration, a capacitor, and an avalanche diode device having a predetermined threshold voltage. Switch means connected between the capacitor and the diode and responsive to the switching pulses couple the capacitor and the diode to the pulse source whereby the capacitor is charged to the reference voltage.

The invention is directed, in a cardiac pacer of the type responsive to a sensed cardiac signal having a desired signal component which exceeds a predetermined amplitude threshold, and operable from a battery supply, to a detector circuit for deriving the signal component. The detector includes first and second differential amplifiers, each having inverting and non-inverting inputs. Means are provided for applying the sensed cardiac signal to the inverting input of the first differential amplifier, and to the non-inverting input of the second differential amplifier. Bias means apply a bias at a first predetermined voltage level to the non-inverting inputs, and reference voltage means apply a reference voltage at a second predetermined voltage level greater than the first predetermined voltage level to the inverting inputs whereby the first differential amplifier produces an output upon the signal component exceeding the difference between the bias and reference voltage levels in one direction, and the second differential amplifier produces an output upon the signal component exceeding the difference between the bias and reference voltage levels in the other direction. The outputs of the differential amplifiers are combined by combining means to form an output signal indicative of the signal component.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

FIG. 6 is a depiction of certain waveforms useful in understanding the operation of the notch filter circuit of FIG. 5a.

DESCRIPTION OF THE PREFERRED EMBODIMENT

Figure 1:
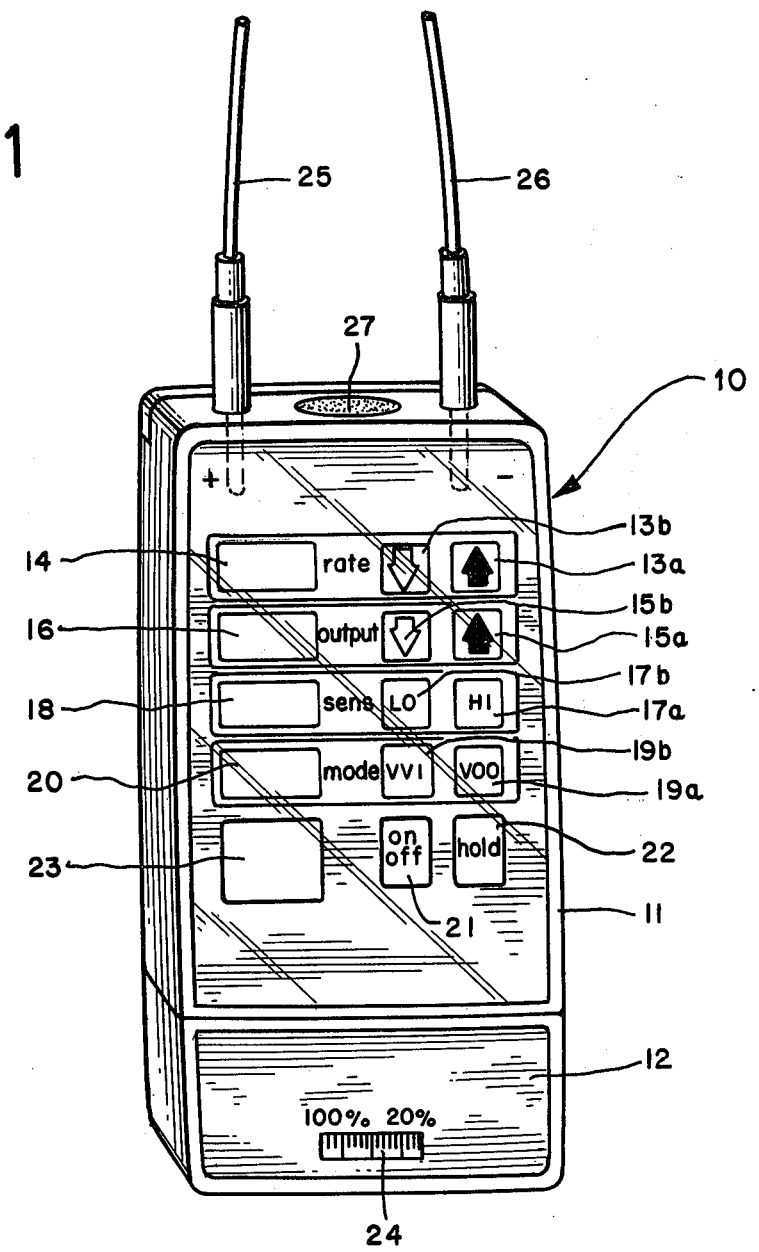
FIG. 1 is a perspective view of an external battery-operated cardiac pacer incorporating the sensing, detection, battery monitor and power supply circuits of the invention.

Referring to the Figures, and particularly to FIG. 1, a portable battery-operated cardiac pacer 10 constructed in accordance with the invention is seen to include a generally rectangular housing 11 having a detachable battery pack 12 of complementary dimensions. The front panel of housing 11 provides various control and indicator functions related to the operation of the pacer. A first pair of increase-decrease push button switches 13a and 13b set output pulse rate. The selected rate, which may range from 30 to 150 pulses per minute in steps of five pulses per minute, is displayed by a liquid crystal display (LCD) 14 positioned to one side of the switches. A second pair of increase-decrease push button switches 15a and 15b select output pulse amplitude. The selected amplitude, which may be either 2, 5, 10, 15 or 20 milliamperes, is displayed by means of a second LCD 16.

The sensitivity level of the pacer is set by means of a pair of high-low select push button switches 17a and 17b. The low sensitivity level may, for example, correspond to a threshold sensitivity level of approximately 2.5 millivolts and the high sensitivity level may, for example, correspond to a threshold sensitivity level of approximately 1.0 millivolts. The selected level is indicated by a third LCD 18.

Cardiac pacer 10 is capable of operating in either a demand mode (VVI), or a free running fixed rate mode (VOO). The particular operating mode is selected by the physician by means of a pair of push button switches 19a and 19b, and is indicated by an LCD 20 arranged to the left (as viewed in FIG. 1) of the mode select switches.

The application of power to the pacer is controlled by an ON-OFF push button switch 21. A push button HOLD switch 22 located to the right of switch 21 must be depressed in order for any of the previously described push buttons, except the pacer ON function, to be operative. Thus, switch 22 serves as an interlock to prevent inadvertent actuation of the other switches and undesired changes to the pacer operating parameters. A fifth LCD 23 located to the left of ON-OFF switch 21 provides an indication of certain specific conditions, such as the presence of noise, the occurrence of a low battery condition, the actuation HOLD switch 22, the sensing of an R-wave, or the production of an output pulse.

To provide an indication of battery life remaining, the removable battery pack 12 may include on its front panel a battery usage indicator 24. This device, which may for example be a coulometer connected to the battery of the pacer so as to be energized during pacer operation, indicates the cumulative usage of the battery, and hence the estimated battery life remaining.

To provide for electrical connection to the heart of a patient, pacer 10 is provided with a pair of pacer leads 25 and 26 which are physically attached to the heart to sense the occurrence of an R-wave upon ventricular contraction, and to stimulate the muscles of the heart into contraction upon the production of a pacer output pulse. The leads, which may be entirely conventional in design and construction, are received in housing 11 by means of an internal pin connector system whereby once inserted the leads are locked in position and cannot be removed until a single release button 27 on the top of the housing is depressed. This connector system is described and claimed in the co-pending application of George Congdon, Ser. No. 210,276, filed Mar. 25, 1982, and assigned to the present assignee.

Figure 2:
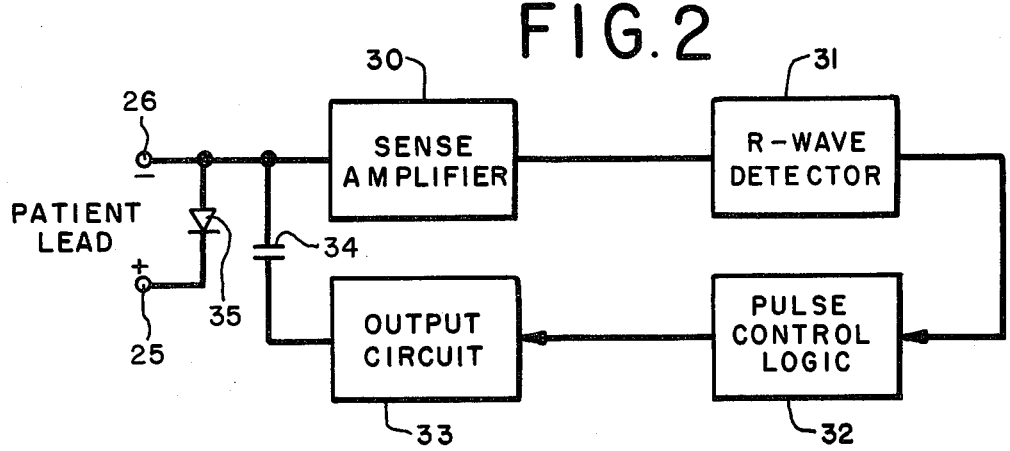
FIG. 2 is a simplified functional block diagram showing the basic operating stages of the pacer.

Referring to FIG. 2, a cardiac pacer 10 in its basic form is seen to include, in accordance with conventional practice, a sense amplifier 30 which amplifies the R-wave conveyed to the pacer by pacer leads 25 and 26. Preferably, amplifier 30 has a bandpass characteristic which attenuates noise and other extraneous signals picked up by pacer leads 25 and 26, so that the detected R-wave may be more effectively amplified for use in the demand mode. The amplified sense signal is applied to an R-wave detector 31, which provides and output pulse upon the occurrence of an R-wave component in the sense signal.

The detector output pulse is applied to a pulse control logic circuit 32, which under appropriate circumstances produces an output control pulse. This control pulse is applied to an output circuit 33 wherein it causes the generation of a pacer output pulse of predetermined amplitude and duration. This pacer output pulse is applied through a capacitor 34 to pacer leads 25 and 26, which convey the pulse to the heart. An avalanche diode 35, connected in reverse-polarity between pacer leads 25 and 26, protects the pacer circuitry from applied high voltage signals.

In a demand operating mode, pulse control logic circuit 32 causes output circuit 33 to produce a pacer output pulse only in the event that an R-wave resulting from natural heart activity is not detected within a selected time period. In an alternate fixed-rate mode, pulse control logic 32 causes the production of pacer output pulses at a rate selected by the user, notwithstanding the presence or absence of R-wave signals at the output of detector 31.

Figure 3:
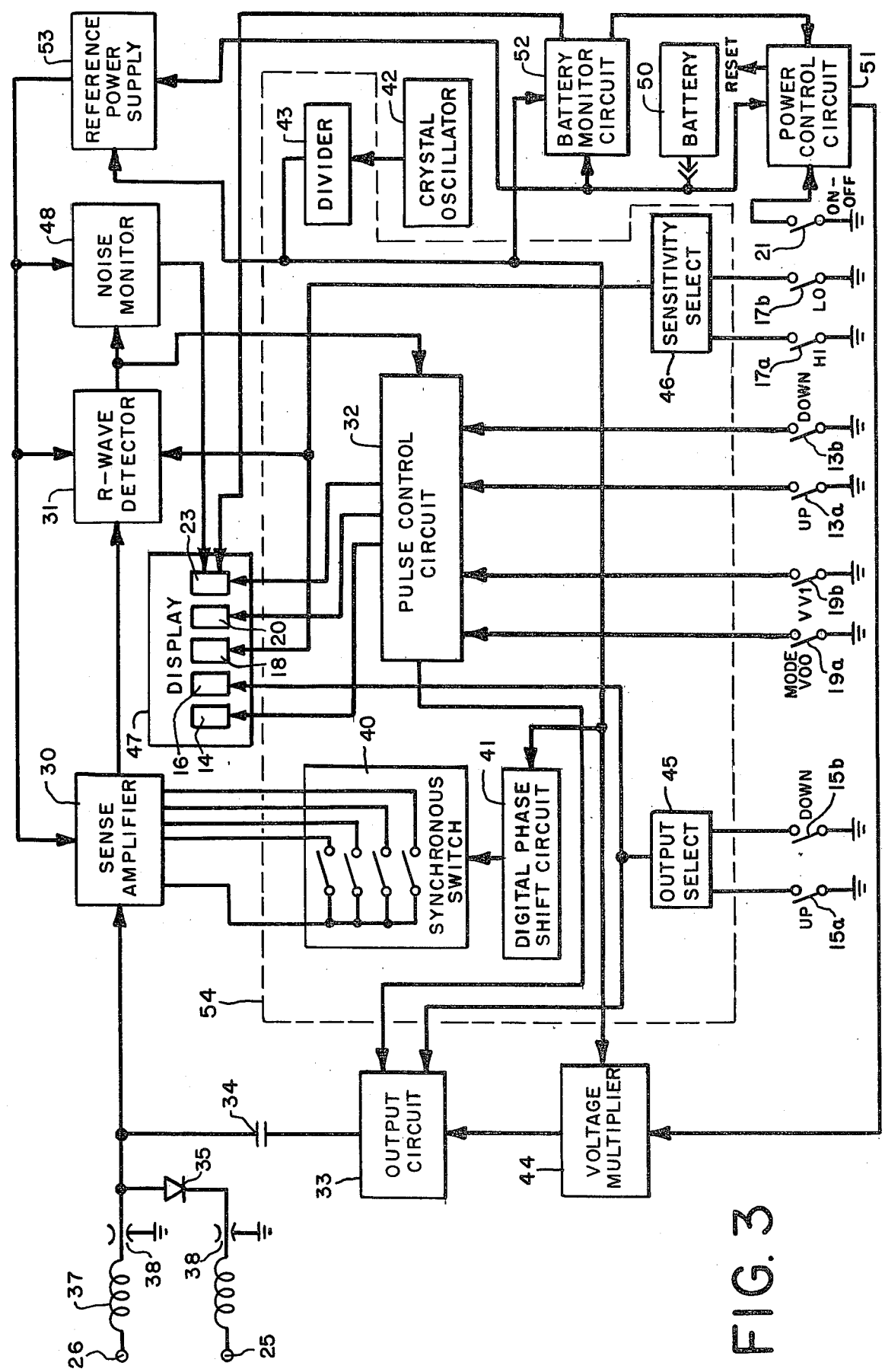
FIG. 3 is a functional block diagram showing the principal stages of the cardiac pacer.

Referring now to FIG. 3, wherein a more detailed functional block diagram of the pacer is shown, it is seen that pacer lead 25 is connected through an inductance 36 to system ground, and that pacer lead 26 is connected through an inductance 37 to the input of sense amplifier 30. Diode 35 is connected between the leads as previously described, and individual feed-through capacitors 38 provide RF bypassing for each lead.

Sense amplifier 30 has associated with it a synchronous switch 40 which, in accordance with one aspect of the invention, enables a synchronous notch circuit to be provided within the amplifier to attenuate power line interference components in the sensed heart signal. Synchronous switch 40 is controlled by the output of a digital phase shift circuit 41, which is driven by the output of a crystal oscillator 42 and frequency divider circuit 43.

The amplified signal from amplifier 30, which contains little or no power line interference as a result of the notch filtering capability of sense amplifier 30, is applied to the R-wave detector 31. This detector compares the amplified sense signal to an applied reference voltage. When the sense signal exceeds this reference, detector 31 produces an R-wave-indicative output signal which is applied to the pulse control logic circuit 32 wherein it determines whether a pacer output pulse is required. In the event that a pacer output pulse is required, logic control circuit 32 produces a control pulse which is applied to output circuit 33. This circuit responds to the control pulse to develop a heart stimulating pulse which is applied to pacer leads 25 and 26 through capacitor 34. To produce the output pulse, output circuit 33 requires a current supply having a voltage level greater than that of the pacer battery, which has a nominal voltage level of 4.2 volts. Accordingly, pacer 10 includes a voltage multiplier circuit 44 which increases the voltage level of the unidirectional current from the pacer battery to a sufficient level for utilization by output circuit 33.

The amplitude of the pulse produced by output circuit 33 is controlled by an output select register 45, which is in turn controlled by push button switches 15a and 15b. Depending on the state of register 45, 1 millisecond pulses of either 2, 5, 10, 15 or 20 milliamperes may be produced.

The operating mode of cardiac pacer 10 is controlled by push button switches 19a and 19b, which connect to pulse control logic circuit 32. Upon momentary actuation of these switches, logic circuit 32 is conditioned to the corresponding operating mode, and LCD 20 is conditioned accordingly. The rate at which output heart stimulation pulses are produced is controlled by switches 13a and 13b, which condition logic circuit 32 to operate at the selected rate, and LCD 14 to provide the appropriate display.

The sensitivity of cardiac pacer 10 to applied R-wave signals is determined by a sensitivity select register 46, controlled by push button switches 17a and 17b. The output of register 46 is applied to R-wave detector 31 to condition that circuit to the selected sensitivity level. At the same time, the sensitivity control signal is applied to LCD 18 to provide an appropriate indication to the operator. LCD 14, LCD 16, LCD 18, LCD 20 and LCD 23 are all part of a display module 47 visible from the front panel of housing 11. It will be appreciated that these devices may be driven in a conventional manner by conventional LCD driven circuitry, not shown in the drawings.

A noise monitor circuit 48, at the output of detector 31, detects the presence of noise at the detector output and conditions LCD 23 to provide a visual warning to the user. At the same time, circuitry within logic circuit 32 reverts to a fixed rate mode in response to the noise to maintain heart activity.

Operating power is supplied to pacer 10 by a battery 50, which may be either an alkaline type battery or a lithium type battery. Supply current from battery 50 is applied to the various circuits of the pacer through a power control circuit 51, which is rendered conductive or non-conductive by user actuation of push button switch 21. At the same time, the output of battery 50 is applied to a battery monitor circuit 52 wherein the battery output voltage is continuously monitored to provide a warning as the battery nears the end of its useful life. This monitoring circuit, which is preferably constructed in accordance with another aspect of the invention, produces an output upon detecting a low battery voltage condition. This is applied to LCD 23 of display module 47. Another output from battery monitor circuit 52 is applied to power control circuit 51 to terminate operation of the pacer should the battery voltage fall below a useful level.

To provide the reference voltage required by R-wave detector 31, pacer 10 includes, in accordance with another aspect of the invention, a pulse-powered reference voltage power supply 53. This power supply provides the required reference voltage, $V_{ref}$, while requiring only a very low current drain, as will be described presently.

In a successful embodiment of cardiac pacer 10, the synchronous switch 40, digital phase shift circuit 41, pulse control logic circuit 32, frequency divider 43, output select register 45, and sensitivity select register 46, together with various other pacer circuit stages are contained on a single CMOS integrated circuit 54. This provides increased reliability in the pacer by obviating the need for discrete circuitry for the included circuit stages.

Figure 4:
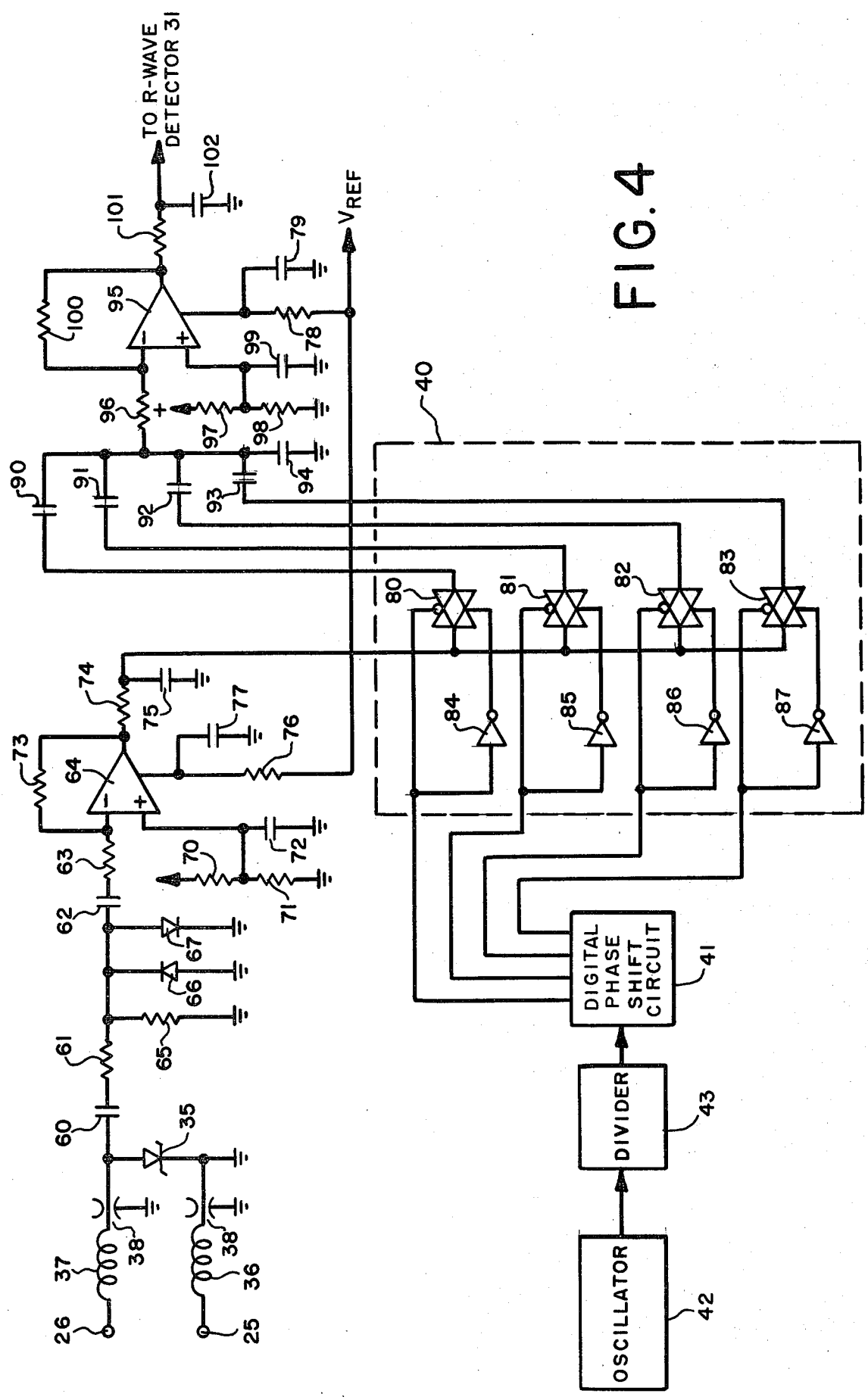
FIG. 4 is a schematic diagram, partially in functional block form, showing the sense amplifier of the pacer.

As previously developed, the sense amplifier 30 of cardiac pacer 10 includes a synchronous active notch filter system for improved attenuation of power line frequency interference. Referring to FIG. 4, the R-wave signal developed by pacer leads 26 and 25 is coupled through the series combination of a capacitor 60 and a resistor 61, and a capacitor 62 and a resistor 63, to the inverting input of a first differential amplifier 64. A resistor 65 and a pair of parallel-connected oppositely-poled diodes 66 and 67 are connected between the juncture of resistor 61 and capacitor 62, and ground to provide peak clipping of the applied signal in a manner well known to the art. Capacitor 60 and resistor 61 form in conjunction with resistor 65 a first highpass filter network, and capacitor 62 and resistor 63 form a second highpass filter network. The effect of these filter networks on the detected heart signal is to attenuate very low frequency components below approximately 15 hertz which have no value to the pacer logic circuitry. In addition, resistor 61 serves as a series impedance during high peak clipping by diodes 66 and 67, as, when large signals are sensed or during the production of an output pulse.

Operating bias is applied to the non-inverting input of differential amplifier 64 by means of a voltage divider comprising a pair of resistors 70 and 71 connected between the pacer voltage supply sourve, $V_{cc}$, and ground. A bypass capacitor 72 is provided to bypass this input to signal currents in a manner well known to the art.

The output of differential amplifier 64 is coupled to the inverting input by a degenerative feedback resistor 73. The output of amplifier 64 is also applied to the synchronous switch 40 through a low pass filter comprising a resistor 74 and a capacitor 75. Operating power is supplied to amplifier 64 by a resistor 76 and a bypass capacitor 77 which connect the amplifier to the reference voltage source $V_{ref}$ of the pacer.

Within the synchronous switch 40, the amplified sense signal is simultaneously applied to four CMOS transmission gates 80-83. Switching control signals are applied to each of these transmission gates by digital phase shift circuit 41 by direct connection to the respective inverting gate of each transmission gate, and by connection through respective inverting amplifiers 84-87 to the non-inverting gate of each transmission gate. As will be seen presently, digital phase shift circuit 41 includes digital circuitry responsive to pulses developed by oscillator 42 and divider 43 to develop short-duration gate control signals which synchronously render transmission gates 80-83 conductive.

The outputs of transmission gates 80-83 are connected to one terminal of respective ones of four storage capacitors 90-93, which together with the transmission gates form four channels for sensing the incoming sense signal. The remaining terminals of capacitors 90-93 are connected to one terminal of a summation capacitor 94, the other terminal of which is grounded, and to the inverting input of a second differential amplifier 95 through a resistor 96. Operating bias is applied to the non-inverting input of differential amplifier 95 by means of a voltage divider network comprising resistors 97 and 98 connected between pacer voltage source $V_{cc}$ and ground, and by a bypass capacitor 99 connected between the non-inverting input and ground. Operating power is supplied to amplifier 95 by a resistor 78 and bypass capacitor 79 which connect the amplifier to the reference voltage source $V_{ref}$ of the pacer.

Degenerative feedback is provided for differential amplifier 95 by a resistor 100 connected between the output and the inverting input of the ampifier. The amplified output signal from amplifier 95 is applied through a lowpass filter network comprising a resistor 101 and a capacitor 102 to the R-wave detector 31 of the pacer.

In operation, transmission gates 80-83 are rendered conductive, one at a time, for short intervals of approximately 28 microseconds at a rate equal to four times the power line frequency, or 240 hertz for 60 hertz applications, and 200 hertz for 50 hertz applications. This causes each channel to sample the interfering power line component at a rate equal to the power line frequency. Consequently, all of the samples of the power line component taken by a particular channel have a magnitude dependent only on the phase angle at which the samples are taken. When the outputs of the channels are combined the DC levels cancel each other and a notch attenuation characteristic at the power line frequency is obtained. The system has the additional advantage of providing notch attenuations at all of the power line harmonics, which may in many applications be present at significant levels.

In order to achieve adequate resolution of the sense signal, a sampling rate higher than the power line frequency is required. In the present embodiment a sampling rate of four times the power line frequency is provided by the four sampling channels, each having a 90 degree phase relationship to the other. It will be appreciated that a greater number of channels may be employed where greater resolution is required.

Figure 5A:
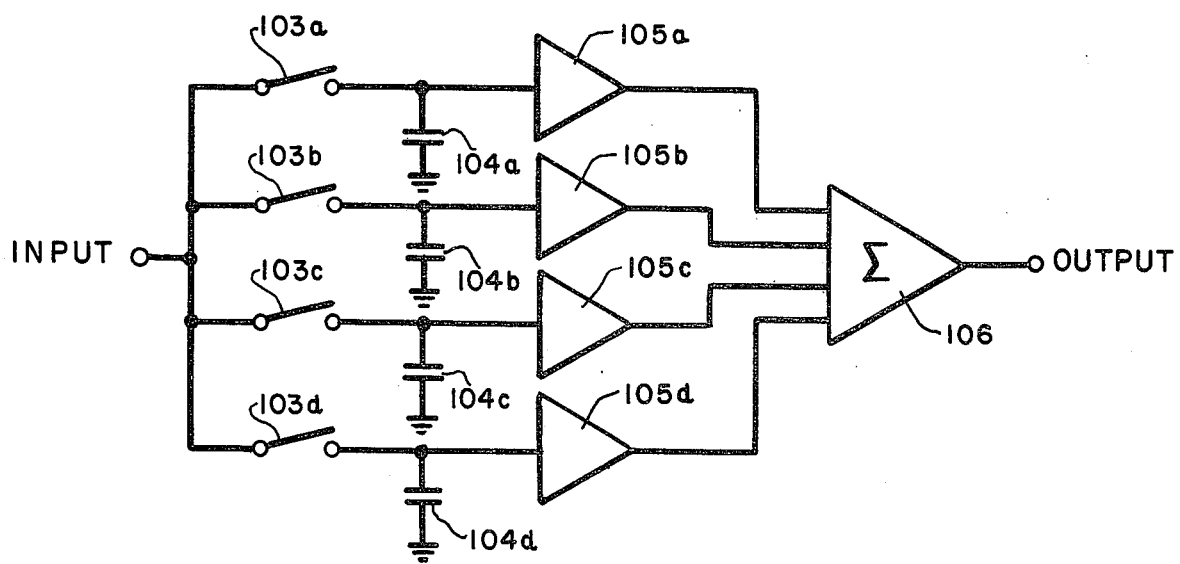
FIG. 5a is a simplified schematic diagram of a notch filter circuit useful in understanding the operation of the invention.
Figure 5B:
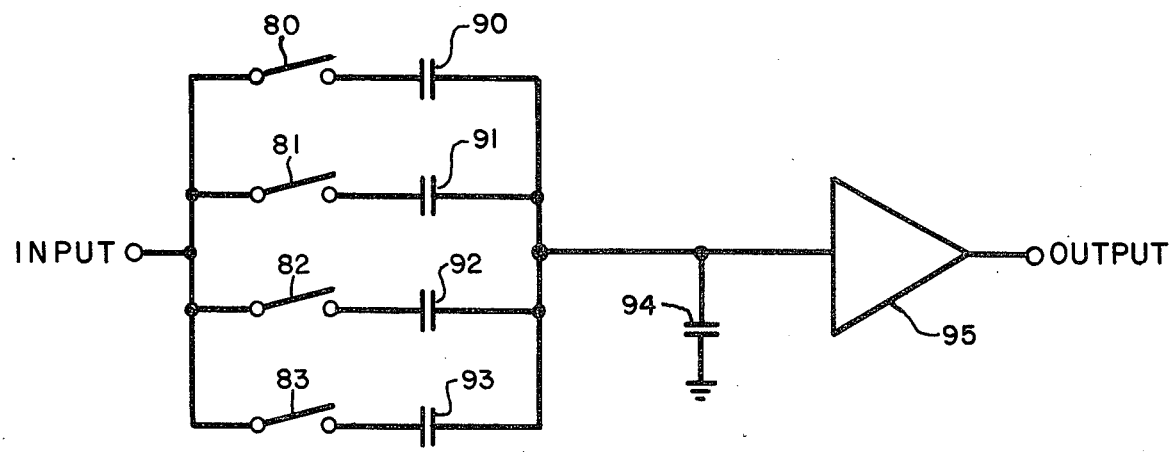
FIG. 5b is a simplified schematic diagram of the notch filter circuit utilized in the pacer.
Figure 6:
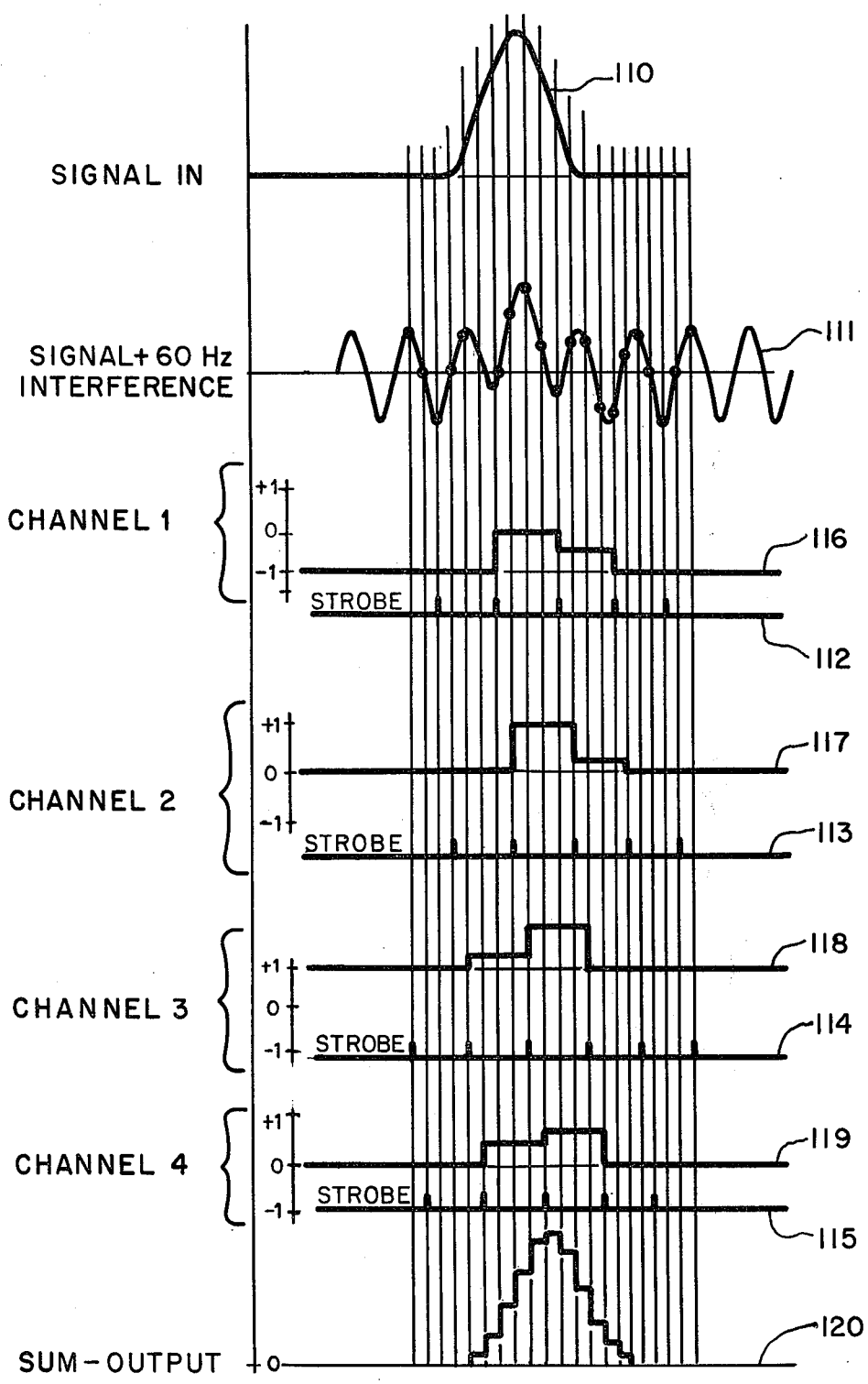

The operation of the notch filter circuit is illustrated in FIGS. 5 and 6. FIG. 5a illustrates a basic four channel system configuration wherein the voltage levels of the four channels are summed to obtain the filtered output signal. The system includes four analog switches 103a-103d, which correspond in function to transmission gates 80-83. These selectively connect the sense signal to four capacitors 104a-104d. The voltage levels across the capacitors are independently applied by four amplifiers 105a-105d, which are summed by a combined amplifier 106 to derive the filtered output signal. The operation of this circuit is graphically illustrated by the waveforms of FIG. 6.

The system configuration shown in FIG. 5b, which corresponds to that of the illustrated pacer embodiment, differs from the configuration of FIG. 5a, in that the charges on the channel capacitors 90-93 are summed by a single capacitor 94. This is advantageous in a battery powered pacer environment, since it obviates the need for individual channel amplifiers, and therefore requires lower power consumption.

In operation, transmission gates 80-83 (FIG. 5b) are strobbed to take a narrow sample of the input signal. This sample is held in a respective hold capacitor. The capacitance of the hold capacitor is limited by the saturated series impedance of the transmission gate (typically several hundred ohms) and the pulse width of the sample strobe (which must be very short compared to the sample rate). For a strobe width of 28 microseconds (typical for this system), hold capacitors 90-93 may be approximately 0.01 microfarads. The channel outputs represented by the charges in capacitors 90-93, are accumulated as a single charge in summing capacitor 94, so that the summed output is represented by a voltage across that capacitor. The amount of charge transferred from capacitors 90-93 is proportional to the magnitude of the voltage difference between the input and the added voltages of the switched capacitors and summing capacitor 94, at the instant the sample is taken.

As previously developed, this method of summing the samples obviates the need for separate buffer amplifiers for each channel, thereby minimizing battery drain. Furthermore, component count is minimized, high circuit impedance levels are avoided, and all of the switched capacitors are the same capacitance so that each channel can be given equal weighting in the summation.

The principle of operation of the notch filter system is illustrated by the waveforms of FIG. 6, which although referenced to a voltage summation as in FIG. 5a, may be taken as applying to a charge summation as shown in FIG. 5b as well. Assuming an R-wave signal as represented by a waveform 110, and that this signal has superimposed thereon an interfering power line frequency component as shown by waveform 111, and that channels 1-4 are periodically sampled in accordance with sampling control signal waveforms 112-115, respectively, then output signals are developed across sample and hold capacitors 90-93 in each channel in accordance with waveforms 116-119, respectively. These sample and hold signals, when summed across capacitor 94, produce waveform 120 which is seen to correspond closely to the desired R-wave input signal. Furthermore, it should be observed that the interfering power line signal produces individual DC components in the four channels as shown, and that these components sum to zero in the output signal. Thus, power line interference is eliminated as a result of the sampling technique.

Figure 7:
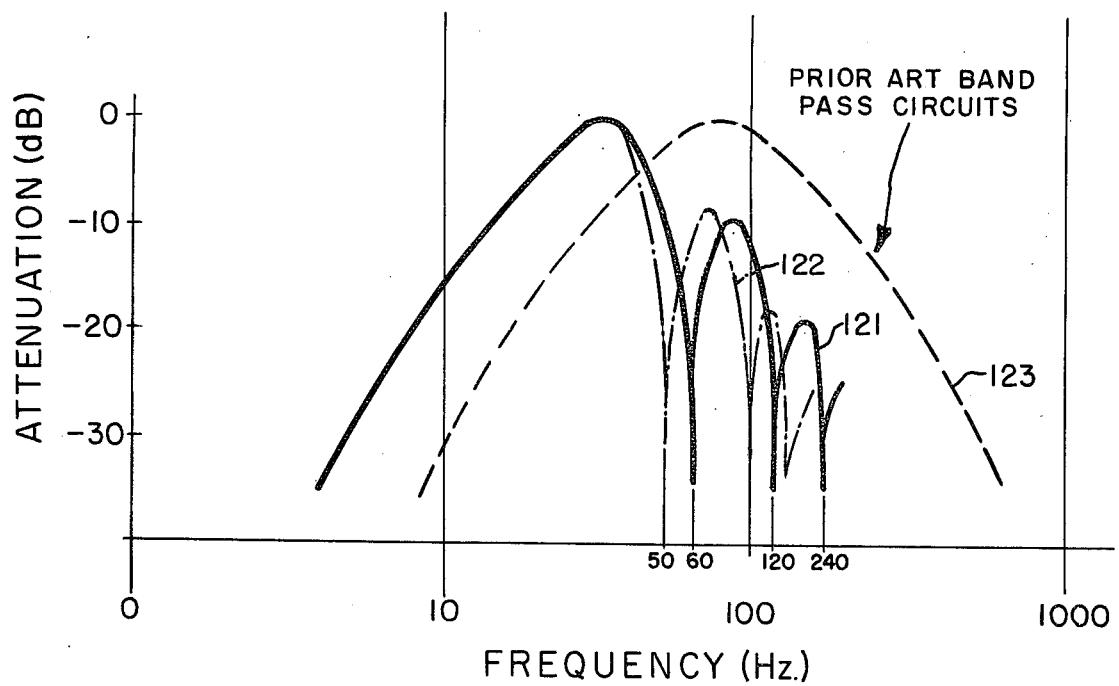
FIG. 7 is a graphical depiction of the bandpass characteristics of the sense amplifier.

The resulting bandpass characteristic of the pacer sense amplifier is illustrated in FIG. 7. Conditioned for 60 hertz interference rejection, with a sampling rate of 240 hertz, a characteristic corresponding to the wavefore 121 is realized. It will be noted that notches exist at the 60 hertz line frequency, and at each harmonic of the line frequency. Furthermore, the passband extends from approximately 15-35 hertz, corresponding to the frequency range of desired R-wave signals. Conditioned for 50 hertz poer line attenuation, as shown by waveform 121, notches exist at 50 hertz and at hermonics of 50 hertz. As with 60 hertz operative, the passband accommodates the 15-35 hertz frequency range of R-wave signals.

In contrast, prior art sense amplifiers incorporating only a conventional bandpass filter, as depicted by waveform 123, did not have a bandpass centered in the 15-35 hertz range, and did not provide attenuation of 60 hertz and 50 hertz power line frequency interference.

For optimum rejection of power line interference, it is necessary that the sampling frequency be accurately controlled. To this end, cardiac pacer 10, in accordance with another aspect of the invention, utilizes crystal oscillator 42 to control the operation of the digital phase shift circuit. For 60 hertz domestic applications, the crystal oscillator operates at 32.640 kHz, and the composite sampling rate is 240.00 hertz, or 60 hertz per channel. For 50 hertz foreign operation, the crystal oscillator operates at 32.800 kHz, and the composite sampling rate is 200.00 hertz, or 50 hertz per channel.

Figure 8:
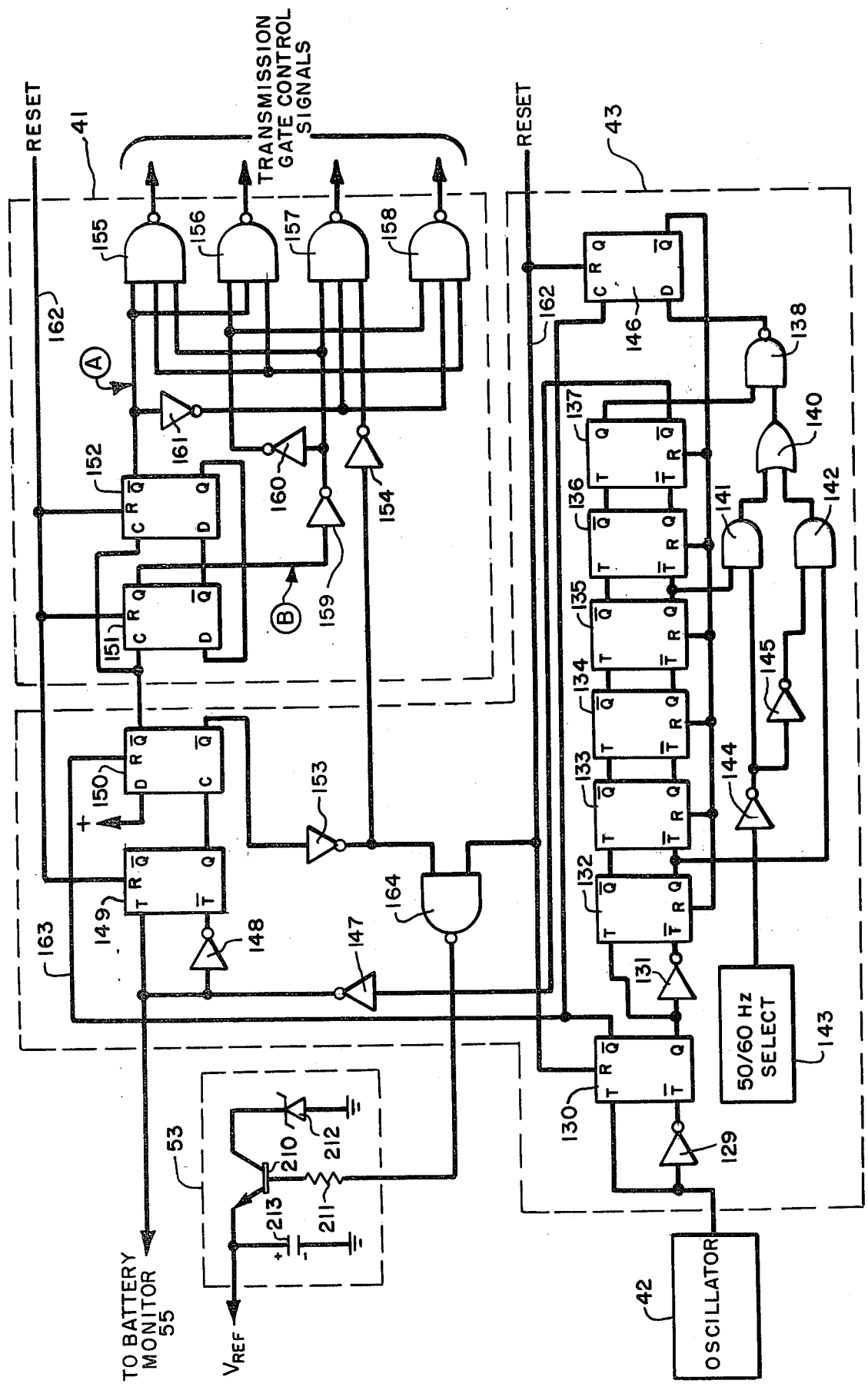
FIG. 8 is a simplified schematic diagram of the digital phase shift and reference voltage circuits of the sense amplifier.

Digital phase shift circuitry for supplying control pulses to transmission gates 80-83 is shown in FIG. 8. The output of oscillator 42, which comprises a highly stable continuous-wave signal, is applied directly and through an inverter 129 to the toggle inputs of a first flip-flop 130, causing this flip-flop to change state in synchronism with the output of the oscillator. The output of flip-flop 131 is applied directly and through an inverter 131 to a frequency divider circuit comprising flip-flops 132-137, these being connected Q output to T input, and Q output to T input, to form a pulse counter in a manner well known to the art. The output of the pulse counter, taken at the Q output of flip-flop 137, is connected to one input of a NAND gate 138. The other input of NAND gate 138 is connected to the output of an OR gate 140, which has one of its inputs connected to the Q output of flip-flop 135 through an AND gate 141, and the other of its inputs connected to the Q output of flip-flop 132 through an AND gate 142. When 50/60 hertz select circuit 143 is conditioned for 60 hertz operation, AND gate 141 is enabled by the select circuit through an inverter amplifier 144. When select circuit 143 is conditioned for 50 hertz operation, the output of the select circuit inhibits AND gate 141 and enables AND gate 142, allowing the Q output of flip-flop 132 to be applied to NAND gate 138 through OR gate 140. In this way, the division factor provided by the pulse counter at the Q output of flip-flop 137 is made dependent on the state of 50/60 hertz selection circuit 143. In practice, a division factor of 82 is provided during 50 hertz operation, with a crystal frequency of 32.800 kHz producing an output signal from the counter of 400.0 hertz, and a division factor of 68 is provided during 60 hertz operation, with a crystal frequency of 32.640 hertz, providing an output signal of 480.0 hertz.

The output of NAND gate 138 is applied to the D input of a D-type flip-flop 146. The C input of this flip-flop is connected to the Q output of flip-flop 130, so that flip-flop 146 is caused to change state following completion of each count. The Q output of flip-flop 146 is connected to the reset inputs of flip-flops 132-137 so that these flip-flops are reset at the end of the count to condition the divider for a subsequent count cycle.

The output of the counter, taken at the Q output of flip-flop 137, is coupled by inverters 147 and 148 to the inputs of a toggle-type flip-flop 149. Consequently, flip-flop 149 divides the applied signal by a factor of two producing an output signal at 240 hertz during 60 hertz operation and at 200 hertz during 50 hertz operation. This output signal is applied to a digital phase shift network comprising three D-type flip-flops 150-152. The D input of flip-flop 150 is biased to a logic high, and the Q output is connected to the C inputs of flip-flops 151 and 152. The Q output of flip-flop 150 is connected through series-connected inverters 153 and 154 to one input of each of four NAND gates 155-158. The Q output of flip-flop 151 is connected through an inverter 159 to remaining inputs of NAND gates 155 and 157, and through an inverter 160 to remaining inputs of NAND gates 156 and 158. The Q output flip-flop 151 is connected to the D input of flip-flop 152. The Q output of flip-flop 152 is connected to remaining inputs of NAND gates 155 and 156, and through an inverter 161 to remaining inputs of NAND gates 157 and 158.

Flip-flops 130, 146, 149, 151 and 152 are reset by reset line 162, which is powered upon initial power-up of the pacer by conventional circuitry within power control circuit 51. A second reset line 163, active with the occurrence of each one-half clock-frequency pulse at the Q output of flip-flop 130, is applied to the reset input of D-type flip-flop 150 to reset that device with each clock pulse, and to the C input of D-type flip-flop 146 to enable a change in output state of that device. As a result, flip-flop 150 is first caused to change state by the 240 hertz (60 hertz operation) pulse from flip-flop 149, and is then reset by the next clock pulse, remaining in its transfer state for the duration of one clock pulse, which for the 32.640 kHz clock frequency has a duration of approximately 30 microseconds. Taking into account other circuit delays, a 240 hertz signal consisting of recurrent pulses of 28 microsecond widths is produced at the Q output of flip-flop 150. These pulses serve as strobe pulses to limit the sampling period of analog switches 80-83.

The outputs of NAND gates 153-156 are applied to respective gate electrodes of transmission gates 80-83 (FIG. 4). The four transmission gates, which may be similar to the type CD4016B quad bilateral switch manufactured by RCA, respond to the outputs of the NAND gates to enable transmission of analog voltage or current signals through the principal electrodes of the transmission gates for the duration of the strobe pulses.

The strobe pulse developed at the output of inverter 147 is also applied to one input of NAND gate 164. The other input of this gate is connected to reset line 162, so that in the absence of a reset strobe, strobe pulses are present at the output of the gate. These reset pulses are utilized by the pulse-operated voltage reference circuit 53 to produce a precise reference voltage with minimal current drain. In the presence of a reset signal, as during initial power-up of the pacer, a continuous logic low output is provided by the NAND gate to bring the reference supply quickly into operation.

Figure 9:
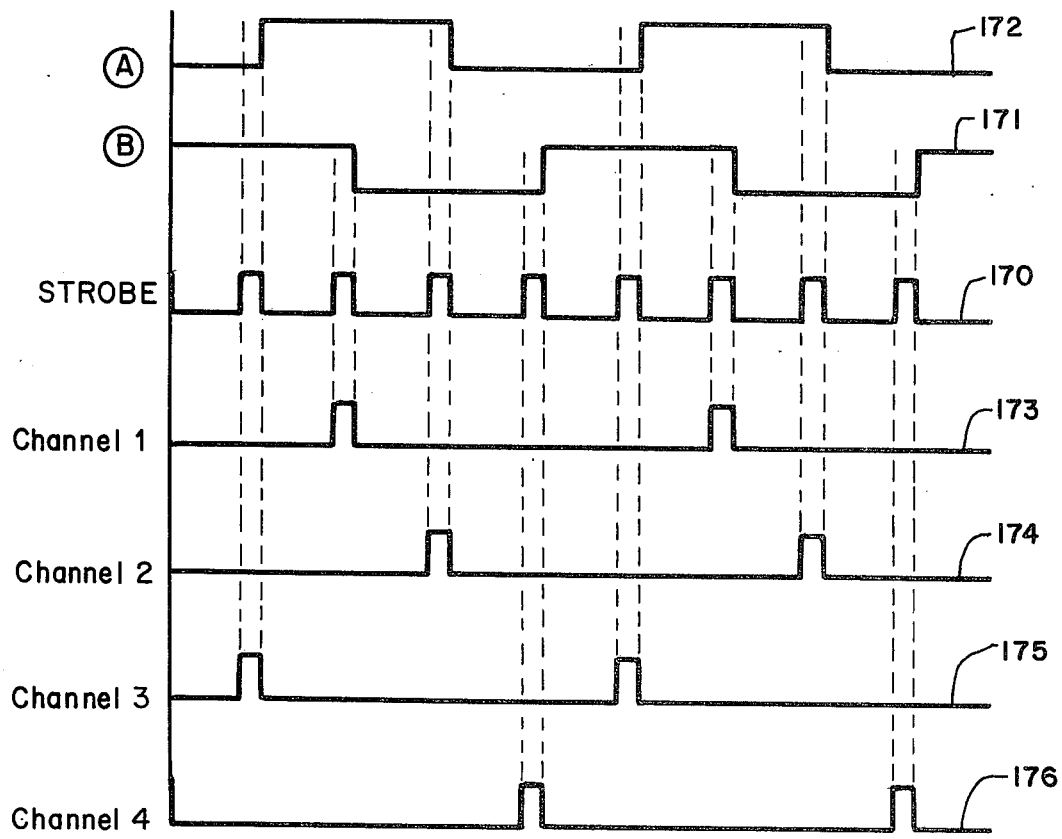
FIG. 9 is a depiction of certain waveforms useful in understanding the operation of the digital phase shift circuit of FIG. 7.

Referring to FIG. 8, in operation the frequency divided output signal from flip-flop 137 causes flip-flop 149 to repetitively toggle, and flip-flop 150 to produce a continuous string of strobe pulses of short duration, typically 28 microseconds. These pulses, which are shown by waveform 170 in FIG. 9, are applied to one input of each of NAND gates 155-158 such that when the other inputs of the NAND gates receive a logic high signal the gates are caused to produce output pulses of short duration. The operation of the NAND gates is further controlled by the Q output of flip-flop 151, as depicted by waveform 171, and by the Q output of flip-flop 152, as depicted by waveform 172. Applied to NAND gates 155-158, these signals cause the NAND gates 155-158 to produce output pulses to analog switches 80-83 in accordance with waveforms 173-176, respectively. Thus, the desired synchronous sampling of the sensed cardiac signal to be accomplished.

Figure 10:
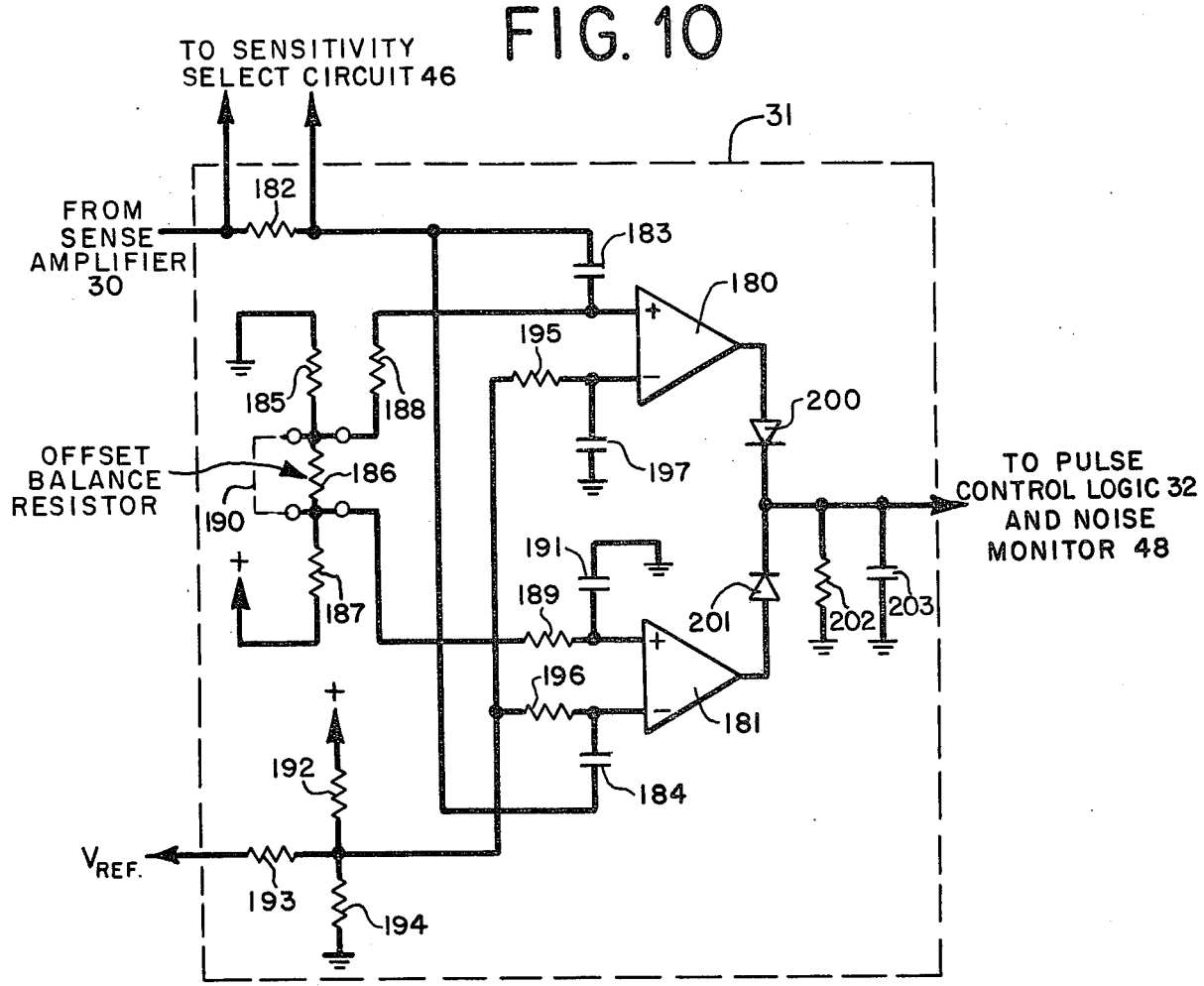
FIG. 10 is a simplified schematic diagram of the R-wave detector of the pacer.

The amplified sense signal from sense amplifier 30 is next applied to R-wave detector 31. Referring to FIG. 10, this detector, in accordance with one aspect of the present invention, includes a first differential amplifier 180 and a second differential amplifier 181 for detecting positive and negative polarity R-wave components in the amplified sense signal. Within detector 31 the amplified sense signal is first applied to a series-connected attenuation resistor 182 which may be selectively switched in and out of the circuit by sensitivity select register circuit 46 in response to user actuation of push button switches 17a and 17b. When not shunted by a transmission gate in register 46, resistor 182 serves to attenuate the sense signal, thereby reducing the sensitivity of the R-wave detector.

The sensed signal is applied to the non-inverting input of differential amplifier 180 through a first coupling capacitor 183, and to the inverting input of differential amplifier 181 through a second coupling capacitor 184. Operating bias is supplied to the non-inverting inputs of the differential amplifiers by means of a voltage divider comprising series-connected resistors 185-187 connected between the pacer voltage supply $V_{cc}$ and ground. The juncture of resistors 185 and 186 is connected by a resistor 188 to the non-inverting input of amplifier 180, and the juncture of resistors 186 and 187 is connected by a resistor 189 to the non-inverting input of amplifier 181. In practice, resistors 185 and 187 may be of equal resistance, and resistor 186 may be shunted by a wire 190 such that resistor 186 is not in the circuit and the non-inverting inputs of the amplifiers both receive the voltage developed at the juncture of the resistors 185 and 187. However, should it be necessary to increase the voltage on one amplifier relative to the other, as when correcting for an imbalance between the amplifiers, the offset balance resistors 188 and 189 may be connected at either the juncture of resistors 185 and 186, or at the juncture of resistors 186 and 187.

The effect of the voltage divider network is to establish at the non-inverting inputs a voltage level corresponding substantially to one-half the nominal operating voltage of the pacer. The amplified sense signal is superimposed on this voltage level by capacitor 183 at the non-inverting input of amplifier 180. The non-inverting input of amplifier 181 is bypassed to ground by a capacitor 191.

A threshold reference voltage is developed for the inverting inputs of differential amplifiers 180 and 181 by a voltage divider comprising resistors 192-194. The output of this voltage divider network, at the juncture of resistors 192-194, is applied to the inverting input of amplifier 180 through a resistor 195, and to the inverting input of amplifier 181 through a resistor 196. The amplified sense signal applied to the inverting input of amplifier 181 is superimposed on the bias thus applied, and the inverting input of amplifier 180 is bypassed to ground by a capacitor 197.

As a result of the application of the reference voltage $V_{ref}$ through resistor 193, which may in practice be a relatively low voltage compared to the supply voltage $V_{cc}$ of the pacer, the reference voltage applied to the inverting inputs of the amplifiers differs from that applied to the non-inverting inputs by a controlled regulated quantity $V_{ref}$. This has the effect of establishing a threshold level in each differential amplifier which, when exceeded by the amplified sense signal, causes the differential amplifier to produce an output. Since the amplified sense signal is applied to the non-inverting input of amplifier 180, this amplifier produces a logic high output upon the non-inverting input being driven higher than the threshold level established on the inverting input. Conversely, since the amplified sence signal is applied to the inverting input of amplifier 181, this amplifier produces a logic high output upon the inverting input being driven below the reference level established on the non-inverting input. Thus, differential amplifier 180 responds to positive-directed signal excursions which exceed the threshold, and differential amplifier 181 responds to negative-directed signal excursions which exceed the threshold level.

The outputs of amplifiers 180 and 181 are coupled through diodes 200 and 201 to the parallel combination of a resistor 202 and capacitor 203 connected to ground. Thus, upon either of the amplifiers being activated a logic high output pulse is developed for application to pulse control logic circuit 32, wherein the generation of output pulses by the pacer is inhibited in the presence of naturally-occurring heart pulses.

If resistors 192-194 of the reference voltage divider are selected to have the same resistance, the threshold voltage $V_t$ applied to differential amplifiers 180 and 181 will be one-half the supply voltage $V_{cc}$ plus one-half $V_{ref}$. For a pacer having a nominal supply voltage of 4.2 volts, and a reference voltage $V_{ref}$ of 1.23 volts, this results in the application of a reference voltage $V_t$ to the amplifiers of 3.2 volts. If resistors 185 and 187 are equal in resistance, and resistor 186 is shorted, then a bias voltage of one-half $V_{cc}$, or 2.1 volts is applied to the other inputs of the amplifiers, and a threshold of one-half $V_{ref}$, or 0.66 volts, must be exceeded by the amplified sense signal in order to be recognized as an R-wave.

Furthermore, if the bias divider network comprising resistors 185-187, and the $V_{cc}$ reference divider network, comprising resistors 192 and 194, provide the same voltage division factor, then the threshold level of the differential amplifier is independent of supply voltage ($V_{cc}$) variations, since these are cancelled out by the circuit. Since in practice the R-wave is substantially greater in amplitude than the other components in the amplified sense signal at the output of the sense amplifier, the R-wave detector produces an output only upon the occurrence of an R-wave.

Capacitor 203 and resistor 202 serve the additional function of detecting noise in the sense signal. Upon the occurrence of noise, the abnormally high repetition rate of the outputs from differential amplifiers 180 and 181 cause the DC voltage level across capacitor 203 to increase to a higher level than obtained at normal repetition rates of detected R-waves. This higher voltage level is recognized by appropriate circuitry within pulse control logic circuit 32 to cause the pacer to revert to a fixed rate mode, and by noise monitor 48, to condition LCD 23 to indicate a noise condition.

Figure 11:
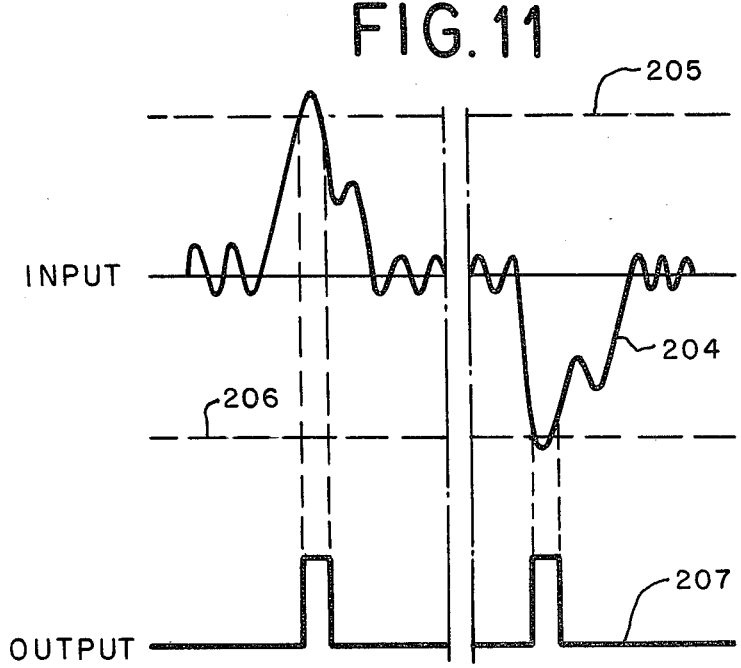
FIG. 11 is a depiction of certain waveforms useful in understanding the operation of the detector circuit of FIG. 9.

The operation of R-wave detector 31 is illustrated in FIG. 11. There it is seen that whenever waveform 204, which represents the amplified sense signal from sense amplifier 30, exceeds a first threshold 205 established by differential amplifier 180, or a second threshold 206 established by differential amplifier 181, the logic high output pulses depicted by waveform 207 are produced. Signals of lesser amplitude, which do not correspond to naturally occurring R-waves, are not detected by detector 31 and do not produce an output. Thus, an output pulse is applied to pulse control logic circuit 32 only upon the occurrence of an R-wave.

In accordance with another aspect of the invention, and with reference to FIG. 5, the reference voltage $V_{ref}$ required by R-wave detector 31 is developed in a reference voltage supply circuit 53 comprising a single bipolar NPN transistor 210. The base of transistor 210 is connected through a resistor 211 to the output of NAND gate 164 of pulse divider circuit 43. The collector of transistor 210 is connected to the anode of an integrated band gap reference device 212, the anode of which is grounded. The emitter of transistor 210 is connected to one terminal of a capacitor 213, the other terminal of which is connected to ground.

In operation, the strobe pulses developed at the output NAND gate 164, which may be at 240 hertz during 60 hertz operation, and at 200 hertz during 50 hertz operation of the pacer, and which may be of 28 microseconds duration, are applied to the base of transistor 210. These pulses cause transistor 210 to be periodically driven into saturation, in effect connecting NAND gate 164 through resistor 211 to the parallel combination of capacitor 213 and reference device 212. The characteristics of device 212 are similar to those of a Zener diode, with the result that the current supplied to capacitor 213 during the 28 microsecond conduction period is limited or clamped at the reference voltage level of the device. Thus, capacitor 213 is charged by the output of NAND gate 164 to the reference level.

During initial power-up the output of NAND gate 164 may comprise a continuous logic low signal for a predetermined interval so that capacitor 213 is more quickly brought up to its operating voltage.

Since the conduction time of transistor 210 is very short, typically having a duty cycle of approximately 0.7%, reference supply circuit 53 has a very low power requirement. However, the reference voltage developed across capacitor 213 is nevertheless continuously available for use by the sense amplifier and R-wave detector circuits of the pacer. In this way, the need for conventional Zener-diode type continuous-drain regulator circuits is avoided and battery life is prolonged.

In one successful embodiment of the reference supply circuit a type 2N5210 transistor was utilized in combination with a 4.7 microfarad capacitor and a type 1CL8069 band gap reference device to obtain a reference voltage level of 1.23 volts. However, it will be appreciated that various other types of avalanche devices, such as Zener diodes, can be utilized instead.

Figure 12:
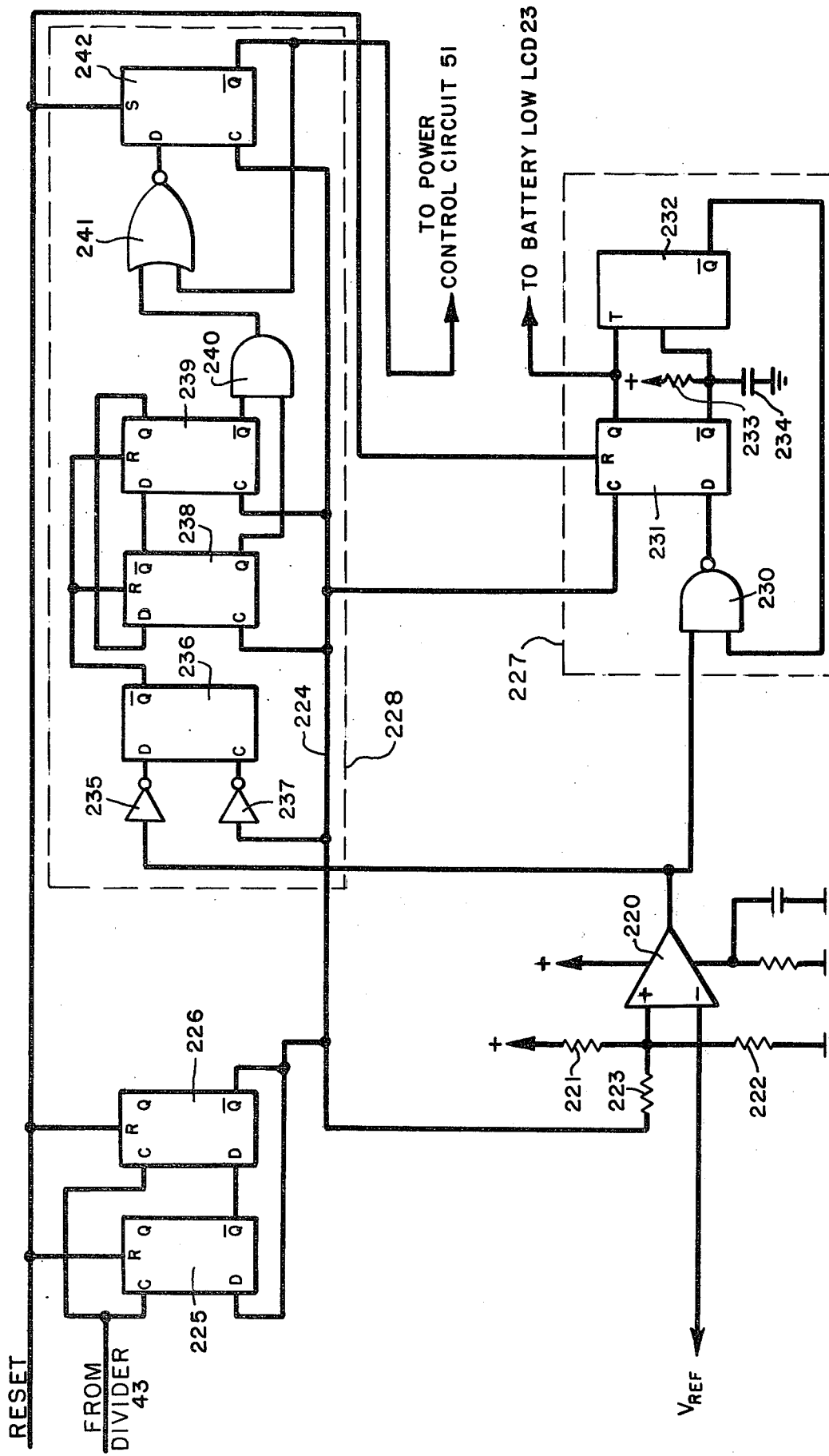
FIG. 12 is a simplified schematic diagram of the battery monitor circuit of the pacer.

In accordance with another aspect of the invention, and with reference to FIG. 12, the condition of the pacer battery 50 is continuously monitored by a battery monitor circuit 52 which includes a single voltage comparator 220. The reference voltage $V_{ref}$ developed by reference voltage supply 53 is applied directly to the inverting input of comparator 220 and serves as a reference level for that device.

A selected portion of the battery supply voltage of the pacer is supplied to the non-inverting input of comparator 220 by a voltage divider network comprising resistors 221 and 222 connected between the operating source and ground. The juncture of resistors 221 and 222 is connected directly to the non-inverting input, and by a resistor 223 to a switching control signal line 224. The effect of the switching control signal on line 224 is to alternately establish ground and $V_{cc}$ connected conditions for resistor 223. In the grounded condition resistor 223 is effectively shunt-connected across resistor 222, causing the voltage divider formed by resistors 221 and 222 to apply a greater percentage of the supply voltage to the non-inverting input of comparator 220. However, when the resistor 223 is taken to $V_{cc}$, resistor 224 is shunt-connected with resistor 221, causing the divider to supply a greater percentage of the supply voltage to comparator 220. As will be seen presently, this principle of operation allows comparator 220 to monitor two different battery voltage conditions.

A switching signal is developed on line 24 by two D-type flip-flops 225 and 226. These flip-flops receive 240 hertz (60 hertz operation) and 200 hertz (50 hertz operation) switching pulses from divider circuit 43 and further divide the received signal by a factor of four to develop a 60 hertz (or 50 hertz) switching control signal. The operation of flip-flops 225 and 226 is entirely conventional in this respect, the received reduced-frequency signal being applied to the C input of flip-flop 225 and the desired switching control signal being developed at the Q output of flip-flop 226.

The output of comparator 220 is simultaneously applied to a battery warning display control circuit 227 and to a pacer power control circuit 228. Within the battery display control circuit 227 the output of comparator 220 is applied to a NAND gate 230. The output of NAND gate 230 is applied to the D input of a D-type flip-flop 231. The C input of flip-flop 231 is connected to switching line 224, so that upon the first positive transition of the switching signal in the presence of an output from comparator 220 flip-flop 231 is switched to a latched condition. The Q output of flip-flop 231 is connected to a monostable multivibrator 232, which in accordance with the RC time constant of a sense-connected resistor 233 and capacitor 234, provides an output after a short predetermined time interval. This output is applied to the remaining input of NAND gate 230, to reset that device following a short time period. The Q output of flip-flop 231 is also connected to a battery low display in LCD 23 to provide an indication of a low battery condition. Once actuated, flip-flop 231 remains in a latched condition until subsequent application of a reset pulse from trigger device 232. If the battery continues to be low, then the device is again latched. The reset terminal of flip-flop 231 may alternatively be connected to a pulse source to obtain a flashing of the display as the flip-flop is repetitively set and reset during a low battery condition.

Within the pacer power control circuit the output of comparator 220 is applied through an inverter 235 to the D input of a D-type flip-flop 236. Switching control line 224 is connected through an inverter 237 to the C input of flip-flop 236, causing that device to periodically change state with changes in the control signal in the presence of an output from comparator 220. The Q output of flip-flop 236 is applied to the reset inputs of a pair of D-type flip-flops 238 and 239 connected as a divide-by-four counter. In accordance with conventional practice, the Q output of flip-flop 239 is connected to the D input of flip-flop 238, the C inputs of the flip-flops are connected to the switching control line 224, and the Q and Q outputs of flip-flops 237 and 239, respectively, are connected to respective inputs of an AND gate 240.

Upon the occurrence of four consecutive positive transitions of the switching control signal on line 224, an output is produced by AND gate 240 and applied to a NOR gate 241. The output of NOR gate 241 is connected to the D input of a D-type flip-flop 242, which is connected as a conventional latch circuit with the Q output of the flip-flop connected to the remaining input of NOR gate 241. The C input of flip-flop 242 is connected to switching control line 224. An output signal suitable for conditioning power control circuit 54 to an off condition is developed at the Q output of flip-flop 242. Once flip-flop 242 has been latched, it remains in a latched condition until the occurrence of a subsequent reset pulse upon subsequent power-up of the pacer.

In operation, when the switching control signal is logic high, the ratio of resistors 221,222 and 223 is such that the voltage applied to the non-inverting input of comparator 220 will fall below the reference voltage $V_{ref}$ supplied to the inverting terminal only when the supply voltage falls below a first predetermined low voltage level, corresponding to an unusable battery. To prevent a transient condition from triggering an unusable battery condition, the output from comparator 220 must occur for four consecutive cycles of the switching signal in order for flip-flop 241 to change state to indicate a dead battery condition.

When the switching control signal is logic low, resistor 222 is partially shunted and $V_{cc}$ does not have to be as low to cause an output from comparator 220. Therefore, a "low battery" condition is tested for, and an output from comparator 220 during this time will result in latching of flip-flop 231 and actuation of the battery low display LCD 23. In one successful embodiment of the battery monitor system employing a lithium battery having a nominal operating voltage of 4.2 volts, the monitor circuit detects a low battery condition at 3.7 volts, and an unusable battery condition at 3.2 volts.

Thus, a cardiac pacer has been shown and described which utilizes novel digital circuitry for achieving a high degree of power line interference discrimination and detection reliability, while maintaining low battery consumption for optimum battery life. The circuitry of the pacer is compact and reliable in operation.

The pacer sense amplifier incorporates a synchronous notch filter system which utilizes the output of the pacer crystal oscillator as a switching signal source to discriminate against interference at power line frequencies. The notch filter may be readily conditioned to operate at a 60 hertz center frequency for use in the U.S., or at a 50 hertz for use in European countries. The output of the sense amplifier is applied to an R-wave detector which utilizes a dual-comparator arrangement for detecting both positive and negative-directed R-waves with a minimal number of components. A pulse-powered reference voltage source comprising a single transistor, capacitor and reference diode develops the required reference voltage for the detector, with minimal power consumption for long battery life.

Pacer battery condition is continuously monitored by a battery monitor circuit which requires only a single comparator, the monitored voltage being alternately attenuated by switching signals derived from the pacer oscillator to achieve battery low warning and battery unusable output indications from a single comparator.

While a particular embodiment of the invention has been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

I claim:

1. In a cardiac pacer of the type responsive to an applied cardiac sense signal which includes a desired signal component and a power line-induced interference component, a sense amplifier comprising:
    means comprising a plurality of selectable sample-and-hold channels for independently sampling the instantaneous amplitude of said cardiac signal;
    sampling means for sequentially and repeatedly selecting said channels whereby each channel is selected for an equal period of time over a complete selecting cycle; and
    signal summation means for combining the outputs of said channels to derive an output signal including said desired signal component;
    said channels being selected at a frequency of nf, where n is a whole integer and f is the frequency of the power line component, whereby said interference component is attenuated from said output signal.

2. A cardiac pacer as defined in claim 1 wherein said sample-and-hold channels each include a signal storage capacitor, and said signal summation means comprise a summing capacitor coupled to each of said signal storage capacitors.

3. A cardiac pacer as defined in claim 1 wherein each of said channels includes an analog switch device, and wherein said sampling means selectively render said switch devices conductive.

4. A cardiac pacer as defined in claim 4 wherein the pacer further includes an oscillator, and wherein said sampling means include frequency divider means, and digital phase shift means for applying the output of said frequency divider means to said analog switch means.

5. A cardiac pacer as defined in claim 1 wherein said sampling period is substantially less than t/K, where t is the duration of one complete sampling cycle, and K is the number of said sample-and-hold channels.

6. In a cardiac pacer of the type responsive to an applied cardiac sense signal which includes a desired signal component and a power line-induced interference component, a sense amplifier comprising:
    means comprising a plurality of selectable sample-and-hold channels each including a signal storage capacitor and an analog switch device for independently sampling the instantaneous amplitude of said cardiac signal;
    sampling means for sequentially and repeatedly rendering said analog switch devices conductive whereby each channel is selected for a predetermined sampling period over each complete selecting cycle;
    signal summation means including a summing capacitor coupled to said signal storage capacitors for combining the outputs of said channels to derive an output signal including said desired signal component; and
    said channels being selected at a frequency of nf, where n is a whole integer and f is the frequency of the power line component, whereby said interference component is attenuated from said output signal.

7. A cardiac pacer of the type responsive to an applied cardiac sense signal which includes a desired signal component and a power line-induced interference component, comprising:
    a continuous-wave signal source;
    pulse control circuit means operable from said continuous-wave signal and responsive to an applied pulse occurrence signal for controlling the production of output pulses from the pacer;
    means comprising a plurality of selectable sample-and-hold channels for independently sampling the instantaneous amplitude of said cardiac signal;
    sampling means operative from said continuous-wave signal source for sequentially and reapeatedly selecting said channels whereby each channel is selected for a predetermined sampling period over each complete selecting cycle;

signal summation means for combining the outputs of said channels to derive a pulse occurrence signal including said desired signal component for application to said pulse control circuit means; and said channels being selected at a frequency of nf, where n is a whole integer and f is the frequency of the power line component, whereby said interference component is attenuated from said pulse occurrence signal prior to application of said pulse occurrence signal to said pulse control circuit means.

8. A cardiac pacer as defined in claim 7 wherein said sampling means include frequency divider means for reducing the frequency of said continuous wave signal, and digital phase shift means for applying the output of said frequency divider means to said analog switch means.

9. A cardiac pacer as defined in claim 8 wherein said sample-and-hold channels each include a signal storage capacitor and an analog switch device, said signal summation means comprise a summing capacitor, and said sampling means individually render each of said analog switch devices conductive.

10. A cardiac pacer as defined in claim 7 wherein said sampling period is substantially less than t/K, where t is the duration of one complete sampling cycle and K is the number of sampling channels.

11. In a cardiac pacer of the type responsive to an applied cardiac sense signal including a desired signal component and a power line-induced interference component, a sense amplifier comprising:

means comprising a plurality of selectable sample-and-hold channels for independently sampling the instantaneous amplitude of said cardiac signal;

sampling means for sequentially and repeatedly selecting said channels whereby each path is selected for a predetermined sampling period once during each complete selecting cycle;

signal summation means for combining the outputs of said channels to derive an output signal including said desired signal component; and said channels being selected for sampling periods substantially less than t/K and at a frequency of nf, where t is the duration of one selecting cycle, K is the number of sample-and-hold hold channels, n is a whole integer and f is the frequency of the power line component, whereby said interference component is attenuated from said output signal.

12. A cardiac pacer as defined in claim 11 wherein said sample-and-hold channels each include a signal storage capacitor, and said signal summation means comprise a summing capacitor coupled to associated ones of said signal storage capacitors.

13. A cardiac pacer as defined in claim 11 wherein each of said channels includes an analog switch device, and wherein said sampling means selectively render said devices conductive.

14. A cardiac pacer as defined in claim 13 wherein the pacer further includes an oscillator, and wherein said sampling means include frequency divider means, and digital phase shift means for applying the output of said frequency divider means to said analog switch means.

* * * * *

UNITED STATES PATENT AND TRADEMARK OFFICE
CERTIFICATE OF CORRECTION

PATENT NO. : 4,436,093
DATED : March 13, 1984
INVENTOR(S) : Kenneth W. Belt

It is certified that error appears in the above-identified patent and that said Letters Patent are hereby corrected as shown below:

```
Col.  8, Line 43:  Change "sourve" to --source--.
Col. 11, Line 21:  Change "Q" to --Q̄--.
         Line 22:  Change "T" to --T̄--.
         Line 39:  Change "Q" to --Q̄--.
         Line 49:  Change "Q" to --Q̄--.
         Line 51:  Change "Q" to --Q̄--.
         Line 55:  Change "Q" to --Q̄--.
         Line 64:  Change "Q" to --Q̄--.
Col. 12, Line  3:  Change "Q" to --Q̄--.
         Line  4:  Change "Q" to --Q̄--.
         Line 13:  Change "Q" to --Q̄--.
         Line 59:  Change "Q" to --Q̄--.
Col. 16, Line 48:  Change "Q" to --Q̄--.
         Line 55:  Change "Q" (second occurrence) to --Q̄--.
         Line 63:  Change "Q" to --Q̄--.
         Line 68:  Change "Q" to --Q̄--.
Col. 18, Line 22:  Change "4" (second occurrence) to --3--.
```

Signed and Sealed this

Sixth Day of November 1984

[SEAL]

Attest:

GERALD J. MOSSINGHOFF

Attesting Officer     Commissioner of Patents and Trademarks